United States Patent [19]

Kline et al.

[11] Patent Number: 5,319,205
[45] Date of Patent: Jun. 7, 1994

[54] PROXIMITY SENSOR FOR GAMMA CAMERA

[75] Inventors: Barry D. Kline, Cleveland Heights; Constantine Fantanas, Grand River; Sarkis Barsamian, Middleburg Heights; Chun Lim, Solon, all of Ohio

[73] Assignee: Trionix Research Laboratory, Inc., Twinsburg, Ohio

[21] Appl. No.: 982,483

[22] Filed: Nov. 27, 1992

[51] Int. Cl.$^5$ .................................................. G01T 1/20
[52] U.S. Cl. ............................ 250/363.04; 250/363.02
[58] Field of Search ...................... 250/363.04, 363.05, 250/363.08, 363.02; 378/4

[56] References Cited

U.S. PATENT DOCUMENTS

| 4,445,035 | 4/1984 | Ueyama | 250/363.04 |
| 4,593,189 | 6/1986 | Stoub | 250/363.04 X |
| 5,055,687 | 10/1991 | Ichihara | 250/363.09 |

Primary Examiner—Constantine Hannaher
Assistant Examiner—Edward J. Glick
Attorney, Agent, or Firm—Pearne, Gordon, McCoy & Granger

[57] ABSTRACT

An imaging detector on a medical imager is provided with a proximity sensor for automatically maintaining a desired distance from the subject to be imaged. The proximity sensor is formed from three infrared beams at decreasing distances from the imaging detector. The imaging detector is moved toward the subject until the first two beams are interrupted. If the third beam is interrupted, the imaging detector is moved back from the subject until only the first beam is interrupted. Faults are detected by monitoring the order in which the beams are interrupted, whether the beams are interrupted when the imaging detector is fully retracted, and whether beams are present when no signal is applied to the beam emitters.

15 Claims, 4 Drawing Sheets 5,319,205

PROXIMITY SENSOR FOR GAMMA CAMERA

BACKGROUND OF THE INVENTION

This invention relates to medical imaging equipment having scanning imaging detectors and, more particularly, to a proximity sensor for controlling the distance between the imaging detector and the subject to be scanned.

In nuclear medicine imaging scans, the imaging detector must often be rotated around or passed over the patient or subject. In the first instance, referred to as SPECT (single photon emission computed tomography), the imaging detector acquires a number of images from various viewing angles around the subject. A computer will later reconstruct from these views a three-dimensional volume representation of the patient's anatomy. A SPECT apparatus is shown in U.S. Pat. No. 5,055,687, which is included herein in its entirety by reference.

In the second instance, referred to as whole body imaging, the detector slowly translates over the subject (or equivalently, the subject is translated past the detector) to generate an image which is much larger than the detector's field of view.

In both of these operations, scanning the detector is necessary as opposed to simple spot viewing of a portion of the subject. In order to maintain the best spatial resolution in the image, the detector must be maintained as close to the subject as practical. Approximately 1 mm of resolution is lost for every additional 1 cm of distance between the detector and the subject.

In order to better follow the contour of the subject, many manufactures of SPECT and whole body scanners permit the operator to "teach" the motion-control hardware or manipulator the trajectory that the detector must take around or over the subject. This is done by manually moving (via hand-operated controls) the detector about the subject. The imaging device memorizes this motion and repeats it during the actually scanning operation.

This teaching operation is performed prior to and in addition to the actual imaging scan of the subject. This is a very time-consuming operation. It increases the labor and machine-time required for a scan, lowers scanner throughput, and requires the subject to be confined to the scanner for a greater time. Particularly in the case of trauma, this delay is undesirable for clinical use.

In addition, the quality of the images obtained is dependent on the technique and skill of individual operators during the teaching process.

SUMMARY OF THE INVENTION

The present invention allows for immediate scanning of a subject. The distance between the subject and the imaging detector is automatically sensed and controlled while the scan itself is in progress.

This saves operator labor which cuts costs. Available machine-time is increased thereby increasing the number of scans that may be scheduled. Time-critical images can be obtained more quickly and subjects need not be confined in the machine as long.

In addition, more reliable and often more accurate images may be obtained because the invention provides consistently repeatable scans in which the distance between the subject and the imaging detector is tightly controlled.

The medical imager includes an imaging detector and a manipulator for providing relative motion between the subject to be imaged and the imaging detector. A proximity sensor is attached to the imaging detector for detecting a distance between the imaging detector and the subject as the subject is scanned by the imaging detector. A controller is included that is responsive to the proximity sensor for controlling the manipulator to maintain a desired distance between the imaging detector and the subject.

The method for maintaining a desired distance between the imaging detector and the subject as the subject is scanned by the imaging detector includes the steps of providing the imaging detector with a proximity sensor, sensing a distance between the imaging detector and the subject with the proximity sensor, and moving the imaging detector and subject relative to each other to maintain the desired distance in response to the sensed distance. In the preferred embodiment, but not necessarily the broadest invention, the proximity sensor includes a beam stack having a first interruptible light beam, a second interruptible light beam and a third interruptible light beam, these beams are at respectively decreasing distances from the imaging detector.

The proximity sensor may be advantageously configured to have a first and a second member extending toward the subject. These members can be moved to a retracted position when not sensing distance.

The desired distance between the imaging detector and the subject is maintained during scanning by moving the imaging detector toward the subject when no beams are interrupted and continuing until the first and second beams are interrupted. If the third beam is interrupted, the imaging detector is moved back from the subject until the second and third beams are no longer interrupted.

A fault condition may be detected if any beam is interrupted out of ascending or descending numerical order.

A fault condition may also be detected if the imaging detector is fully retracted from the subject and a beam is interrupted.

If the light beams are each produced by an emitter and detected by a respective light detector, a fault condition may also be detected if any light detector detects a light beam when the light detector's respective emitter is not emitting.

In the preferred embodiment, the medical imager includes an imaging detector having a subject-facing surface and a manipulator for providing relative motion between the subject and the imaging detector. An emitter stack is attached to the imaging detector near the perimeter of the surface and a light detector stack is attached to the imaging detector near the perimeter opposite the emitter stack.

A first, second and third light emitter is located in the emitter stack, each emitter being respectively closer to the surface. A first, second and third synchronous light detector is located in the light detector stack, each light detector being respectively closer to the surface. The light detector provides a continuous series of synchronizing pulses and a signal indicative of a detected light beam. The respective emitters and light detectors are aimed at each other.

A controller receives the synchronizing pulses and selectively applies a subset of the synchronizing pulses to respective emitters. The respective emitters emit light in pulses synchronized with the subset. The controller also receives the beam indicating signals and controls the manipulator to maintain a desired distance between the imaging detector and the subject in response to the beam indicating signals.

In the preferred embodiment, the controller successively applies at least three synchronizing pulses from each light detector to respective emitters and the light detectors require at least three synchronized light pulses from respective emitters before providing a beam indicating signal.

The controller periodically blocks the synchronizing pulses from the emitters and if any of the beam indicating signals are received, the controller detects a fault condition.

DESCRIPTION OF THE PREFERRED EMBODIMENT

Figure 1:
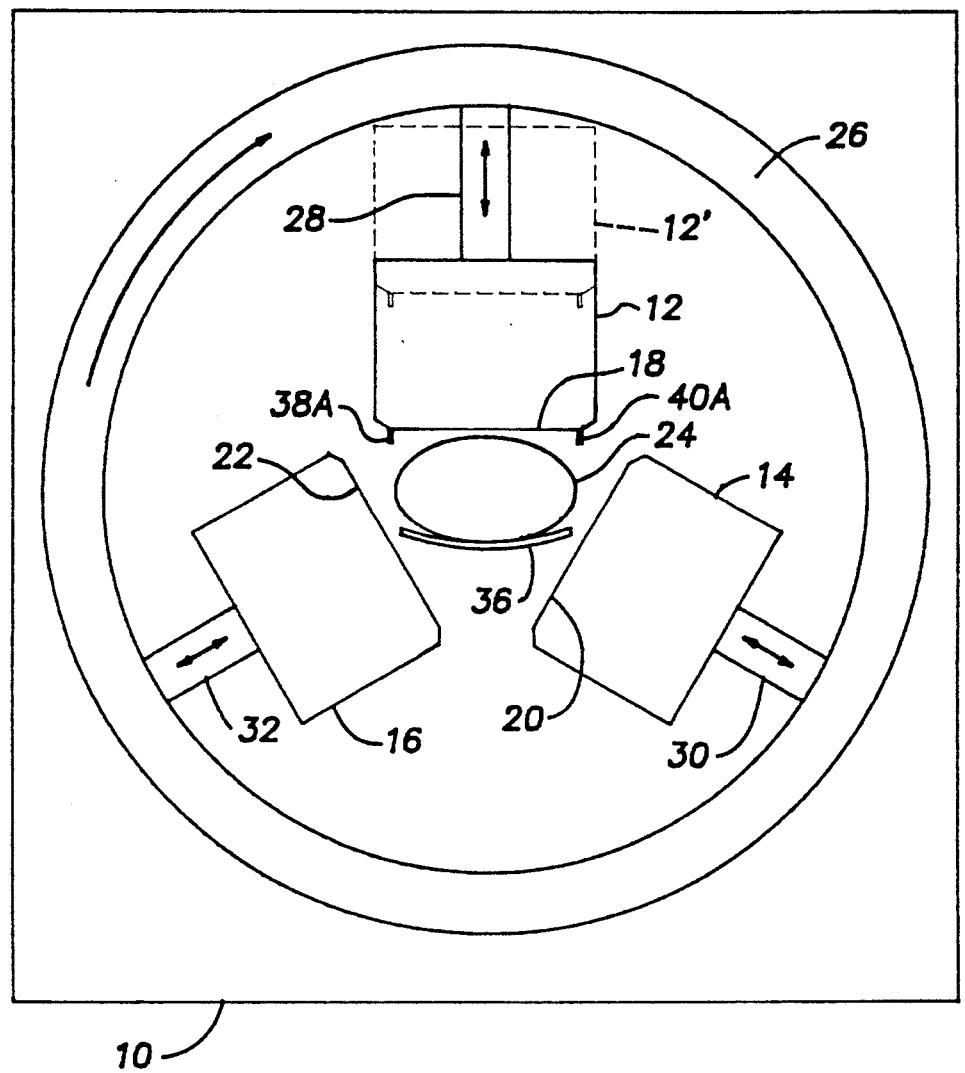
FIG. 1 is a cross sectional axial elevation view of a gamma camera according to the invention.

Referring to FIG. 1, a SPECT medical imager 10 has three heads 12, 14, 16. The heads 12, 14, 16 each have a respective imaging detector 18, 20, 22 facing a subject 24. The imaging detectors 18, 20, 22 detect imaging data from the subject 24 which is then used to produce images of the subject 24. While a three-head imager is described, the invention may also be practiced with other numbers of heads.

The heads 12, 14, 16 are attached to a ring 26 by respective radial supports 28, 30, 32. During the imaging process the heads 12, 14, 16 rotate with the ring 26 about the subject 24. Each head 12, 14, 16 can be translated radially toward or away from the subject 24 along the respective supports 28, 30, 32.

The fully retracted position of the head 12 is indicated by the numeral 12'.

The subject 24 is supported by a support 36 cantilevered from an unshown base.

Figure 2:
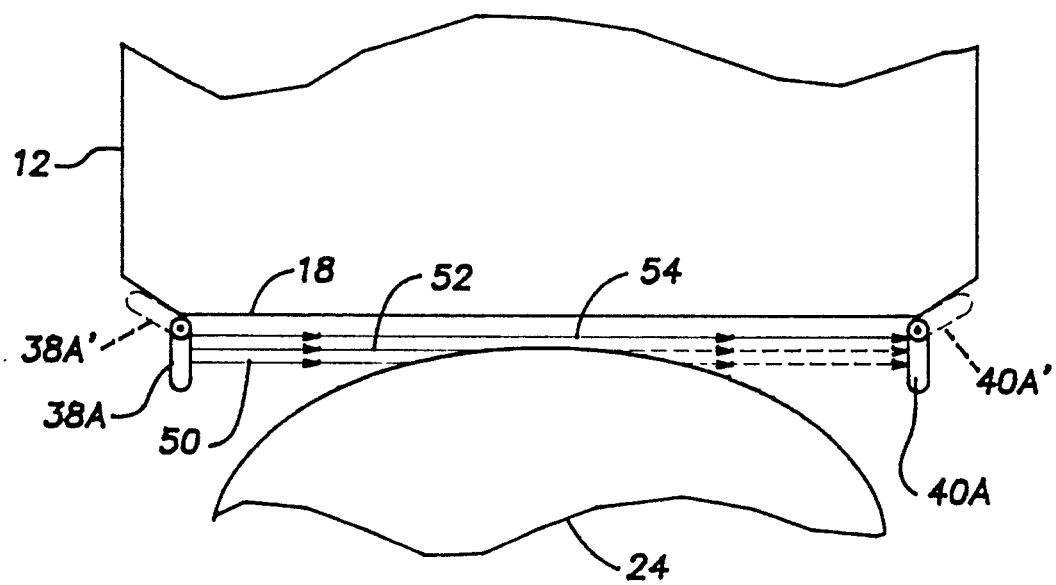
FIG. 2 is an enlarged portion of FIG. 1 showing a proximity detector according to the invention.
Figure 3:
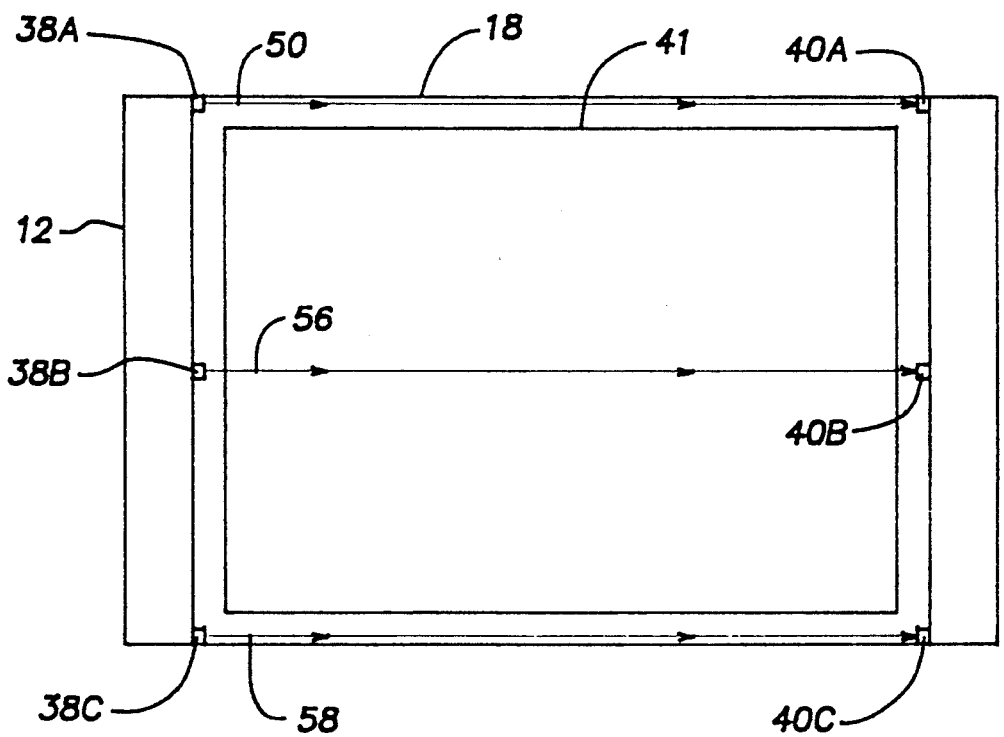
FIG. 3 is a bottom plan view of the imaging detector of FIG. 2.

Referring to FIGS. 2 and 3, the head 12 is provided with three emitter stacks 38A, 38B, 38C and three detector stacks 40A, 40B, 40C. The emitter stacks 38A, 38B, 38C are mounted near the perimeter of the imaging detector 18. The detector stacks 40A, 40B, 40C are mounted near the perimeter of the imaging detector 18 opposite the emitter stacks 38A, 38B, 38C, respectively.

A pressure-sensitive or contact switch 41 is provided on the surface of the imaging detector 18.

The stacks 38A, 38B, 38C, 40A, 40B, 40C are each hinged to the head 12 so that they may be retracted or folded out of the way as exemplified by the positions indicated by numerals 38A' and 40A'. This allows the heads 12, 14, 16 to move closer together when imaging a small subject 24 where the minimum distance between the detectors 18, 20, 22 and the subject 24 is dictated by the size of the heads 12, 14, 16 and detectors 18, 20, 22.

Each emitter stack 38A, 38B, 38C contains three light 19 emitters, which may be, for example, infrared light-emitting diodes (LED). Each detector stack 40A, 40B, 40C contains three light detectors, which may be, for example, synchronous light detectors such as Hamamatsu Photonics Model No. S4282-11.

Figure 4:
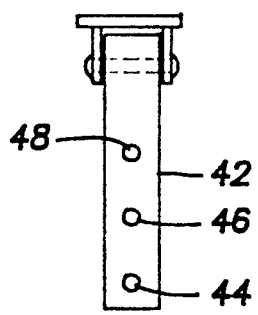
FIG. 4 is an exemplary side elevation view of a stack housing in enlarged scale.

Referring to FIG. 4, an exemplary stack housing 42 is advantageous the same whether used as an emitter stack or a detector stack. In the case of the emitter stacks 38A, 38B, 38C, the positions 44, 46, 48 are occupied by emitters. In the case of the detector stacks 40A, 40B, 40C, the positions 44, 46, 48 are occupied by detectors. The positions 44, 46, 48 are located below the surface of the detector 18 at respectively closer distances.

Respective pairs of emitters and detectors face each other to establish beams as exemplified by the light beams 50, 52, 54 in FIG. 2 and the light beams 50, 56, 58 in FIG. 3. All of the beams are mutually parallel and parallel to the surface of the imaging detector 18. The outside beam 50 may be, for example, 2 cm from the imaging detector 18; the middle beam 52 may be, for example, 1.5 cm from the imaging detector 18; and the "too close" beam 54 may be, for example, 1 cm from the imaging detector 18. The beams associated with the stacks 38B, 40B and the stacks 38C, 40C have a similar spacing from the detector 18.

While three pairs of emitter and detector stacks are described, other numbers of pairs may be used, for example, one pair or five pairs.

The Hamamatsu detector is optimized for infrared detection. It supplies a continuous series of synchronizing pulses for energizing an LED. Each pulse received by the LED causes the LED to emit a light pulse in synchronism with the synchronizing pulse. By synchronizing its detection of light to its synchronizing pulses, the detector is able to detect the LED's light in conditions of high background illumination and noise.

When the Hamamatsu detector detects three light pulses in a row synchronized to its synchronizing pulses, it provides a signal indicating that it has detected a light beam.

Figure 5:
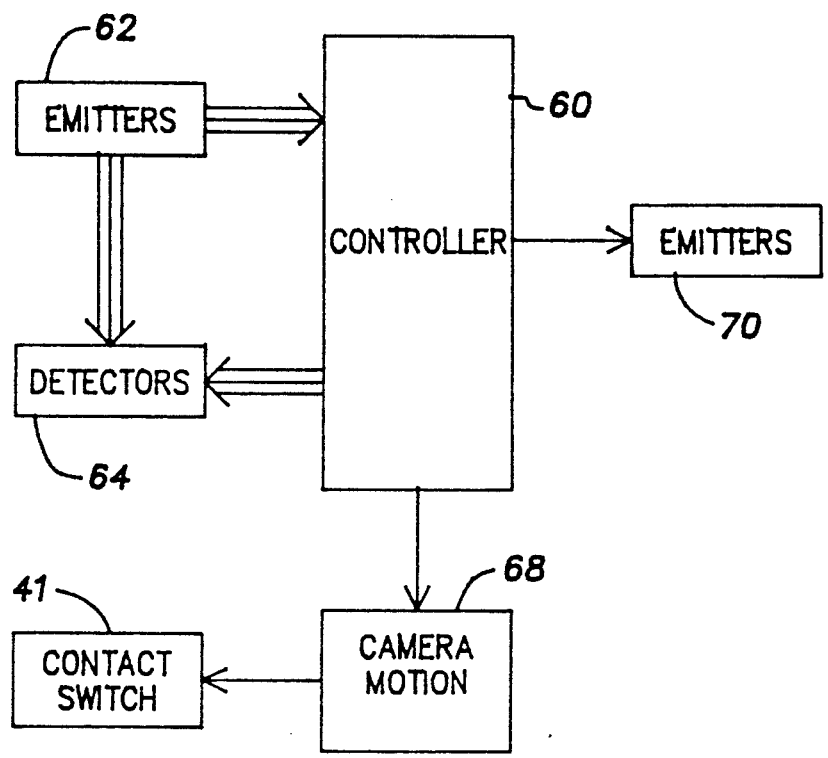
FIG. 5 is a block diagram of a proximity sensor according to the invention.

Referring to FIG. 5, a controller 60 supplies drive pulses to the emitters 62. These drive pulses, may be advantageously derived from a subset of the synchronizing pulses from the detectors 64. For example, five synchronizing pulses from each detector in turn may be applied to each detector's respective emitter. In this way, only one emitter is energized at a time and for five synchronizing pulses. This produces five light pulses which should be sufficient for the detector to produce a signal indicating a detected beam if nothing obstructs the beam.

If a light beam is detected, the detectors 64 provide the controller 60 with a signal indicating which beam has been detected.

The controller 60 provides a signal to the camera motion control 68 to control the radial translation of the head 12.

The controller 60 receives a signal from the camera motion control 68 when the head 12 is in the fully retracted position 12'.

The contact switch 41 provides a signal to the camera motion control 68 indicative of contact between the head 12 and the subject 24.

The controller provides a fault signal 70 upon detection of a fault condition.

Figure 6:
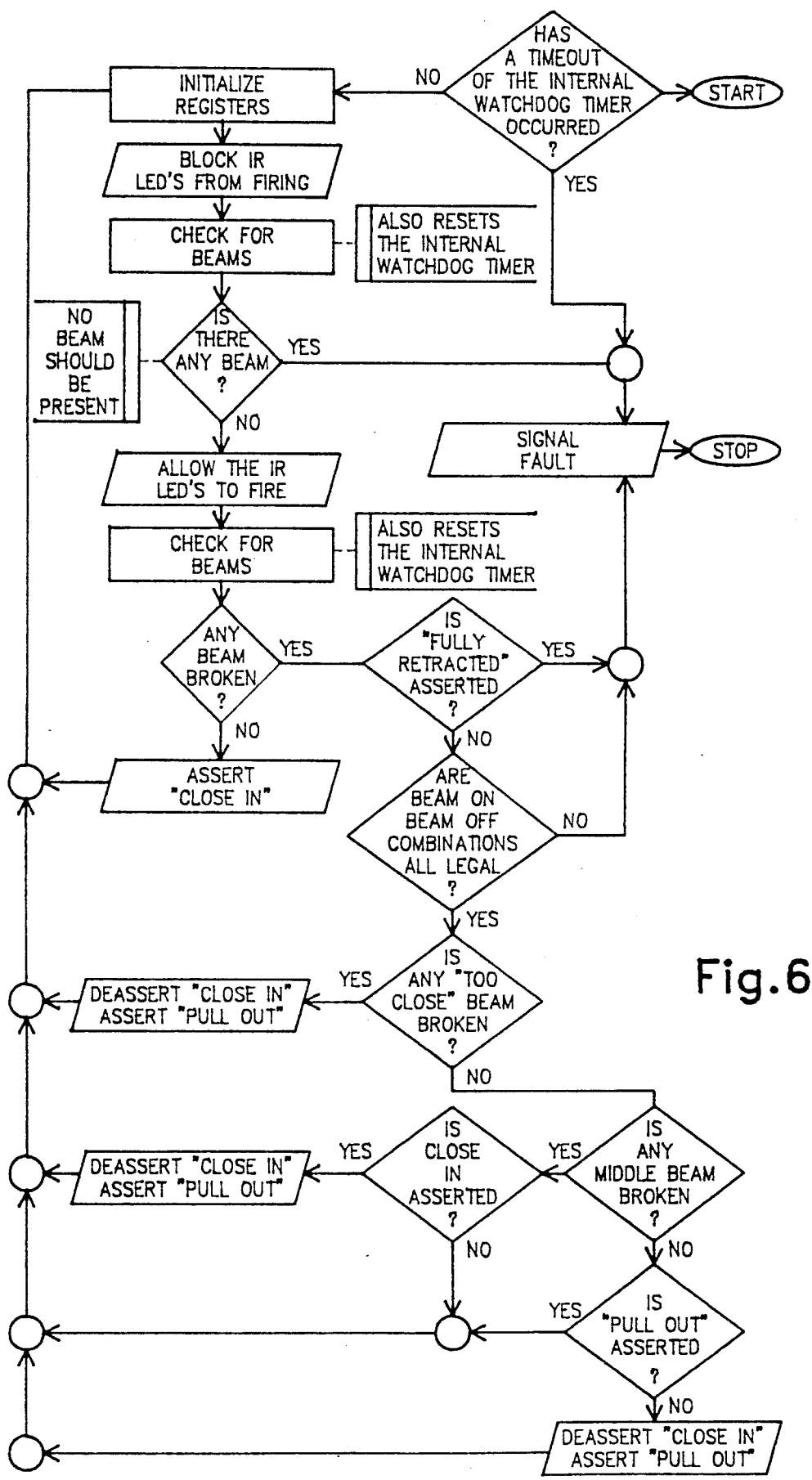
FIG. 6 is a flow chart diagram of a proximity sensor according to the invention.

Referring to FIGS. 2 and 6, the operation of the imager 10 includes the known process of scanning the imaging detectors 18, 12 20, 22 around the subject 24. In addition, in order to move the imaging detector 18 to within a desired distance from the subject 24, the controller 60 instructs the camera motion control 68 to move the head 12 towards the subject 24.

The head 12 closes in until an outside and middle beam is interrupted on one of the stack pairs 38A/40A, 38B/40B, 38C/40C e.g., the beams 50, 52).

The controller 60 then instructs the camera motion control 68 to stop translating the head 12 (the rotational scan continues).

If one of the "too close" beams is interrupted (e.g., the beam 54), the controller 60 instructs the camera motion control 68 to move the head 12 back from the subject 24.

The head 12 pulls out until all of the "too close" and middle beams are uninterrupted.

The controller 60 then instructs the camera motion control 68 to stop translating the head 12 (the rotational scan continues).

In this manner a desired distance is maintained between the imaging detector 18 and the subject 24 corresponding to a distance between the "too close" beam distance and the outer beam distance (e.g., 1-2 cm).

Because no translation of the head 12 occurs when the distance is in this range, chattering is eliminated, thereby improving the longevity and reliability of the motion control components.

In the preferred embodiment, the camera motion control 68 causes the heads 14, 16 to follow the same trajectory as the head 12. As an alternative, each head can be equipped with proximity sensors and operated independently.

The controller 60 also periodically blocks all of the synchronizing pulses and check for any beams. If a beam is detected, a fault condition is detected and a fault signal 70 is generated.

The controller 60 also checks for the presence of the beams when the fully retracted signal is present from the camera motion control 68. If all beams are not detected, a fault condition is detected and a fault signal 70 is generated.

The controller 60 also checks for "illegal" combinations of beams. This includes, for example, such situations as a middle beam interrupted before the respective outside beam has been interrupted, or if the three beams are numbered sequentially, the beams are interrupted or restored out of ascending or descending order, respectively. If an "illegal" combination is detected a fault condition is detected and a fault signal 70 is generated.

If the contact switch 41 indicates that the head 12 has contacted the subject 24, the camera motion control 68 retracts all the heads 12, 14, 16 and indicates a fault condition.

While a light beam proximity detector has been described, it is also possible to practice the invention with other types of proximity detection, for example, ultrasonic or radio frequency sensing.

Also, while the automatic distance control of the invention has been described with respect to a SPECT imager, it is equally applicable to a whole body scanner (translational versus rotational). The invention may also be applied to spot imaging.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A medical imager for imaging a subject, said imager comprising:
    an imaging detector;
    a manipulator for providing relative motion between said subject and said imaging detector;
    a proximity sensor operably connected to said imaging detector for detecting a distance between said imaging detector and said subject as said subject is scanned by said imaging detector, said proximity sensor including a beam stack having a first interruptible light beam, a second interruptible light beam and a third interruptible light beam, said beams being at respectively decreasing distances from said imaging detector; and
    a controller responsive to said proximity sensor for controlling said manipulator to maintain a desired distance between said imaging detector and said subject.

2. A medical imager according to claim 1, wherein said proximity sensor comprises a plurality of beam stacks having mutually parallel beams.

3. A medical imager according to claim 1, wherein said proximity sensor includes a first and a second member extending toward said subject, said members being movable to a retracted position when not sensing distance.

4. A method for maintaining a desired distance between an imaging detector and a subject as the subject is scanned by the imaging detector, the method comprising:
    providing the imaging detector with a beam stack having a first interruptible light beam, a second interruptible light beam and a third interruptible light beam, said beams being at respectively decreasing distances from said imaging detector;
    moving said imaging detector toward said subject when no beams are interrupted and continuing until said first and second beams are interrupted; and
    moving said imaging detector back from said subject when said third beam is interrupted and continuing until said second and third beams are no longer interrupted.

5. A method according to claim 4, further comprising detecting a fault condition if any beam is interrupted out of ascending or restored out of descending numerical order.

6. A method according to claim 4, further comprising sensing if said imaging detector is fully retracted from said subject and detecting a fault condition if any beam is interrupted contemporaneously with said full retraction.

7. A method according to claim 4, wherein said light beams are each produced by an emitter and detected by a respective light detector, said method further comprising detecting a fault condition if any light detector detects a light beam when a respective emitter of said any light detector is not emitting.

8. A method according to claim 4, further comprising providing said imaging detector with a pressure-sensitive switch and detecting a fault condition if said switch contacts said subject.

9. A medical imager for imaging a subject, said imager comprising:

an imaging detector having a subject-facing surface, said surface having a perimeter;

a manipulator for providing relative motion between said subject and said imaging detector;

an emitter stack attached to said imaging detector near said perimeter;

a light detector stack attached to said imaging detector near said perimeter opposite said emitter stack;

a first, second and third light emitter in said emitter stack, each emitter being respectively closer to said surface;

a first, second and third synchronous light detector in said light detector stack, each light detector being respectively closer to said surface and being adapted to provide a continuous series of synchronizing pulses and a signal indicative of a detected light beam, the respective emitters and light detectors being aimed at each other; and a controller receiving said synchronizing pulses and selectively applying a subset of said synchronizing pulses to respective emitters thereby causing said respective emitters to emit light in pulses synchronized with said subset, receiving said beam indicating signals, and controlling said manipulator to maintain a desired distance between said imaging detector and said subject in response to said beam indicating signals.

10. A medical imager according to claim 9, wherein said controller successively applies at least three synchronizing pulses from each light detector to respective emitters and said light detectors require at least three synchronized light pulses from respective emitters before providing a beam indicating signal.

11. A medical imager according to claim 9, wherein said controller periodically blocks said synchronizing pulses from said emitters and if any of said beam indicating signals are received, said controller detects a fault condition.

12. A medical imager according to claim 9, wherein said controller directs said manipulator to move said imaging detector toward said subject when all beam indicating signals are received and to continue said movement toward the subject until the first and second beam indicating signals are no longer received, and said controller directs said manipulator to move said imaging detector back from said subject when no beam indicating signals are received and to continue said movement back from the subject until only the first beam indicating signal is no longer received.

13. A medical imager for imaging a subject, said imager comprising:

an imaging detector;

a manipulator for providing relative motion between said subject and said imaging detector;

a proximity sensor operably connected to said imaging detector for detecting a distance between said imaging detector and said subject as said subject is scanned by said imaging detector, said proximity sensor including a beam stack having at least a first interruptible light beam and a second interruptible light beam, said beams being at respectively decreasing distances from said imaging detector; and a controller responsive to said proximity sensor for controlling said manipulator to maintain a desired distance between said imaging detector and said subject.

14. A medical imager according to claim 13, wherein said proximity sensor comprises a plurality of beam stacks having mutually parallel beams.

15. A medical imager according to claim 13, wherein said proximity sensor includes a first and a second member extending toward said subject, said members being movable to a retracted position when not sensing distance.

* * * * *